United States Patent [19]

Nakamura et al.

[11] Patent Number: 5,638,821
[45] Date of Patent: Jun. 17, 1997

[54] ULTRASOUND DIAGNOSTICS SYSTEM FOR OBTAINING A TOMOGRAPHIC IMAGE

[75] Inventors: Yasuhiro Nakamura, Kanagawa-ken; Seiji Aoki, Kawasaki, both of Japan

[73] Assignee: Matsushita Electric Industrial Co., Ltd., Osaka, Japan

[21] Appl. No.: 602,644

[22] Filed: Feb. 16, 1996

[30] Foreign Application Priority Data

May 26, 1995 [JP] Japan ................................. 7-127863

[51] Int. Cl.$^6$ ............................... A61B 8/00; G01N 29/00
[52] U.S. Cl. ........................................ 128/661.01; 73/625
[58] Field of Search ...................... 128/661.01, 660.07, 128/660.01, 661.09; 73/625, 626

[56] References Cited

U.S. PATENT DOCUMENTS

| | | | |
|---|---|---|---|
| 4,423,737 | 1/1984 | Yano et al. | 128/661.01 |
| 4,813,279 | 3/1989 | Shirasaka | 73/626 |
| 5,060,652 | 10/1991 | Umemura et al. | 128/661.01 |
| 5,072,735 | 12/1991 | Okazaki et al. | 128/660.07 |
| 5,113,706 | 5/1992 | Pittaro | 73/626 |
| 5,143,075 | 9/1992 | Ishizuka | 128/661.01 |
| 5,379,642 | 1/1995 | Reckwerdt et al. | 128/661.01 X |

FOREIGN PATENT DOCUMENTS

0087318  8/1983  European Pat. Off. .

*Primary Examiner*—Francis Jaworski
*Attorney, Agent, or Firm*—Lowe, Price, LeBlanc & Becker

[57] ABSTRACT

A plurality of groups of delay time data corresponding to a plurality of focal distances Fn satisfying a condition that a ratio $(F_i - F_{i-1})/(F_{i-1} - F_{i-2})$ is equal to a constant value higher than one are stored in a focus memory. Therefore, the groups of delay time data corresponding to short focal distances are densely stored. When a particular focal distance is specified, a plurality of ultrasonic pulses delayed according to a particular group of delay time data corresponding to the particular focal distance are transmitted from a plurality of micro-piezoelectric transducers to a focal point of an organism at the particular focal distance. Thereafter, a plurality of echo signals reflected at the focal point of the organism are received by the micro-piezoelectric transducers, and a piece of tomographic image data indicating a portion of a tomographic image is produced in a signal processing unit. Therefore, in cases where one or more particular focal distances are specified, pieces of tomographic image data indicating a tomographic image are produced according to one or more particular group of delay time data, and the tomographic image is displayed according to the tomographic image data.

11 Claims, 5 Drawing Sheets

ULTRASOUND DIAGNOSTICS SYSTEM FOR OBTAINING A TOMOGRAPHIC IMAGE

BACKGROUND OF THE INVENTION

1. Field of the Invention

The present invention relates to an ultrasound diagnostics system for obtaining a tomographic image of an organism by transmitting a plurality of ultrasonic pulses to the organism at a focal distance and receiving a plurality of echo signals reflected on the organism while scanning the organism.

2. Description of the Related Art

2.1. Previously Proposed Art

A tomographic image of an organism is obtained by using an ultrasound diagnostics system in which ultrasonic pulses are transmitted to an organism at a focal distance and receiving a plurality of echo signals reflected on the organism while scanning the organism.

Figure 1:
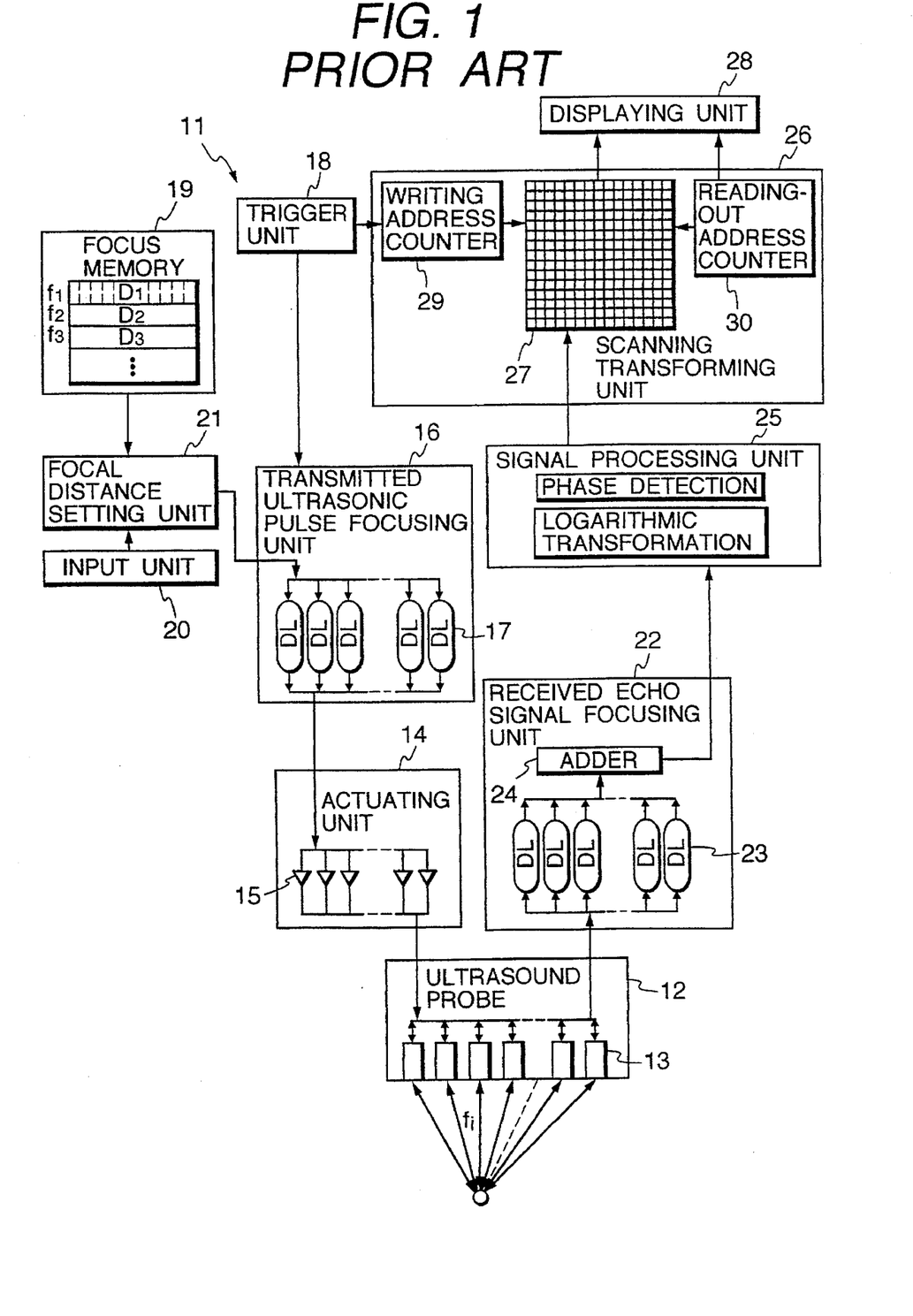
FIG. 1 is a block diagram of a conventional ultrasound diagnostics system.

FIG. 1 is a block diagram of a conventional ultrasound diagnostics system.

As shown in FIG. 4, a conventional ultrasound diagnostics system 11 comprises an ultrasound probe 12 having a plurality of micro-piezoelectric transducers 13 for transmitting a plurality of ultrasonic pulses from the transducers 13 to an organism while scanning the organism and receiving a plurality of echo signals reflected in the organism to the transducers 13, an actuating unit 14 having a plurality of pulse oscillators 15 for actuating the micro-piezoelectric transducers 13 of the ultrasound probe 12 with a plurality of actuating pulses transmitted from the pulse oscillators 15, a transmitted ultrasonic pulse focusing unit 16 having a plurality of delaying circuits 17 for transmitting a plurality of delaying pulses Tx generated in the delaying units 17 to the pulse oscillators 15 to delay the generation of the actuating pulses for the purpose of converging the ultrasonic pulses transmitted from the micro-piezoelectric transducers 13 to a focal point of the organism, a trigger unit 18 for transmitting a trigger pulse Tg to the transmitted ultrasonic pulse focusing unit 16 to trigger the generation of the delaying pulses Tx, a focus memory 19 for storing a plurality of groups of delay time data Dn (n=1 to N) corresponding to a plurality of focal distances fn, an inputting unit 20 for inputting a piece of input information indicating a desired focal distance fi, a focal distance setting unit 21 for reading a group of delay time data Di from the focus memory 19 according to the input information and transmitting the group of delay time data Di to the transmitted ultrasonic pulse focusing unit 16 to set the convergence of the ultrasonic pulses at a focal point of the organism corresponding to the focal distance fi, a received echo signal focusing unit 22 having a plurality of delaying circuits 23 and an adder 24 for delaying the echo signals transmitted from the micro-piezoelectric transducers 13 of the ultrasound probe 12 at a plurality of time differences in the delaying circuits 23 to converge the echo signals at a fixed time and adding the echo signals together in the adder 24 to produce a summed echo signal Se, a signal processing unit 25 for performing a logarithmic transformation for the summed echo signal Se obtained in the received echo signal focusing unit 22 and detecting a phase of the summed echo signal Se to produce a piece of tomographic image data indicating a portion of a tomographic image, a scanning transformation unit 26 having two-dimensional memories 27 for writing the piece of tomographic image data transmitted from the signal processing unit 25 in each of the two-dimensional memories 27 according to a scanning line of the ultrasonic pulses and producing an image signal Sv indicating the tomographic image expressed by a displaying format such as a television format, and a displaying unit 28 for displaying the ultrasound tomographic image of the organism according to the image signal Sv transmitted from the two-dimensional memories 27.

In the above configuration, an operation in the conventional ultrasound diagnostics system 11 is described.

A group of micro-piezoelectric transducers 13, a group of pulse oscillators 15, a group of delaying circuits 17 and a group of delaying circuits 23 respectively correspond to a plurality of channels, and an operation among the ultrasound probe 12, the actuating unit 14, the transmitted ultrasonic pulse focusing unit 16 and the received echo signal focusing unit 22 is performed for each of the channels.

When an operator inputs a piece of input information indicating a desired focal distance fi, a group of delay time data Di corresponding to the focal distance fi is read out by the focal distance setting unit 21, and a delaying pulse Tx is generated in each of the delaying circuits 17 according to the group of delay time data Di in the pulse focusing unit 16 in synchronization with a trigger pulse Tg transmitted from the trigger unit 18. Thereafter, an actuating pulse is generated in each of the pulse oscillators 15 when the delaying pulses Tx are received by the actuating unit 14 at different times, and the micro-piezoelectric transducers 13 of the ultrasound probe 12 are actuated by the actuating pulses. Therefore, a plurality of ultrasonic pulses delayed by prescribed different times are output from the transducers 13, and the delayed ultrasonic pulses simultaneously reach a focal point of an organism corresponding to the focal distance fi. That is, the delayed ultrasonic pulses are converged at the focal point of the organism.

Thereafter, an echo signal reflected at the focal point of the organism is generated for each of the delayed ultrasonic pulses, and the echo signals are received by the transducers 13 at prescribed different times. Thereafter, the echo signals are delayed in the delaying circuits 23 of the received echo signal focusing unit 22 and are added up together in the adder 24 to produce a summed echo signal Se. Thereafter, in the signal processing unit 25, the summed echo signal Se is logarithmic-transformed, and the transformed signal is phase-detected in amplitude modulation to produce a piece of tomographic image data. Therefore, pieces of tomographic image data indicating a portion of tomographic image on a scanning line can be produced by the signal processing unit 25 when the group of ultrasonic pulses is transmitted to a plurality of focal points of the organism along the scanning line at the desired focal distance fi. The pieces of tomographic image data are transmitted one after another to the scanning transformation unit 26.

In the unit 26, each of the tomographic image data is written in a corresponding two-dimensional memory 27. In this case, an address of the corresponding two-dimensional memory 27 is indicated by an address signal output from a writing address counter 29 to which the trigger pulse Tg of the trigger unit 18 is input. Therefore, the pieces of tomographic image data are written in a memory region of the two-dimension al memories 27 corresponding to the desired focal distance fi in synchronization with the trigger pulses Tg. Therefore, when a group of ultrasonic pulses is transmitted to the organism at each of a plurality of focal distances, pieces of tomographic image data indicating a frame of tomographic image are produced by the signal processing unit 25 and are written in all of the two-dimensional memories 27 of the scanning transformation unit 26.

Thereafter, the tomographic image data stored in the two-dimensional memories 27 are read out one after another according to address signals output from a reading-out address counter 30 and are transformed to a format such as a television format represented by the National Television System Committee. The tomographic image data indicating the tomographic image expressed by the television format are output to the displaying unit 28. Also, a synchronizing signal is output from the address counter 30 to the displaying unit 28. Therefore, the tomographic image is displayed in synchronization with the synchronizing signal by the displaying unit 28.

Figure 2A:
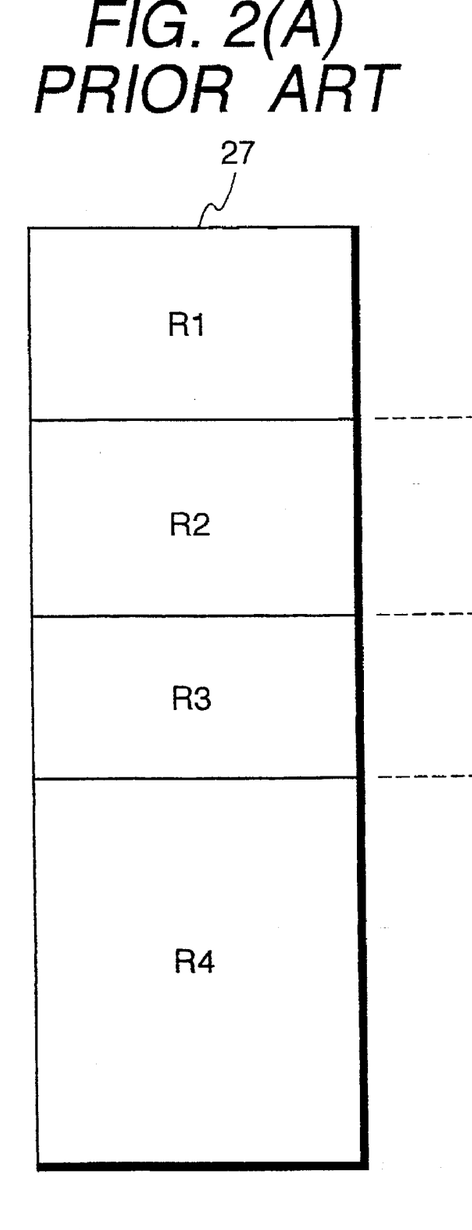
FIG. 2(A) shows two-dimensional memories, shown in FIG. 1, divided into four memory regions.

FIG. 2(A) shows the two-dimensional memories 27 divided into four memory regions R1 to R4.

In cases where pieces of tomographic image data corresponding to only one focal distance f1 are produced in the ultrasound diagnostics system 11, the tomographic image data indicating one tomographic image corresponding to the focal distance f1 are written in the entire four memory regions R1 to R4 of the two-dimensional memories 27. Also, in cases where pieces of tomographic image data corresponding to a first focal distance f1 and a second focal distance f2 larger than the first focal distance f1 are produced in the ultrasound diagnostics system 11, the tomographic image data indicating a part of tomographic image corresponding to the first focal distance f1 are written in the first and second memory regions R1 and R2 of the two-dimensional memories 27, and the tomographic image data indicating a remaining part of tomographic image corresponding to the second focal distance f2 are written in the third and fourth memory regions R3 and R4 of the two-dimensional memories 27. Therefore, one tomographic image corresponding to the focal distances f1 and f2 is obtained. Also, in cases where pieces of tomographic image data corresponding to four focal distances f1 to f4 (f1<f2<f3<f4) are produced in the ultrasound diagnostics system 11, the tomographic image data indicating a first part of tomographic image corresponding to the first focal distance f1 are written in the first memory region R1, the tomographic image data indicating a second part of tomographic image corresponding to the second focal distance f2 are written in the second memory region R2, the tomographic image data indicating a third part of tomographic image corresponding to the third focal distance f3 are written in the third memory region R3, and the tomographic image data indicating a fourth part of tomographic image corresponding to the fourth focal distance f4 are written in the fourth memory region R4. Therefore, one tomographic image corresponding to the four focal distances f1 to f4 is obtained.

Figure 2B:
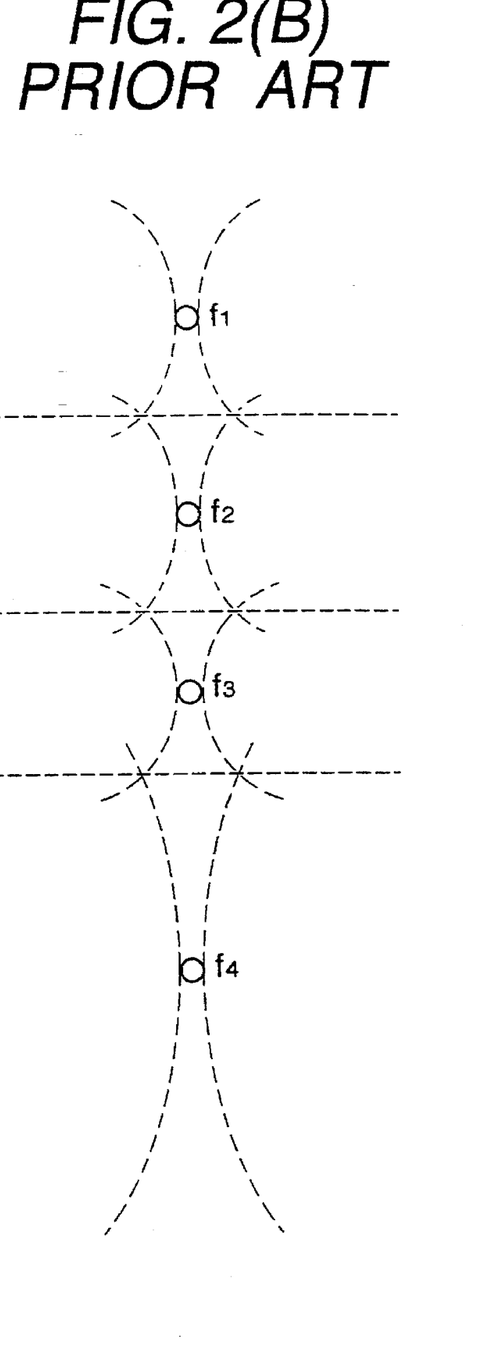
FIG. 2(B) shows a beam width and a beam intensity in a beam of ultrasonic pulses converged which vary with a converging depth.

As shown in FIG. 2(B), a beam width and a beam intensity in a beam of the ultrasonic pulses converged by the transmitted ultrasonic pulse focusing unit 16 varies with the focal distance fi (or a converging depth). Therefore, a position of each boundary line between two memory regions adjacent to each other is determined to almost equalize a beam width and a beam intensity corresponding to one memory region with those corresponding to the other memory region at the boundary line.

Also, when an operator focuses the ultrasonic pulses on a remarked focal point of the organism to produce a tomographic image corresponding to one focal distance or two or more focal distances, one group of delay time data or a combination of two or more groups of delay time data is selected by inputting a piece of input information to the input unit 20 by the operator.

Therefore, a plurality of groups of delay time data Dn corresponding to the focal distances fn are stored in advance in the focus memory 19, one group of delay time data or a combination of two or more groups of delay time data is selected, and the ultrasonic pulses are converged at a remarked focal point of the organism. Accordingly, a tomographic image having a superior focus orientation resolution can be obtained in the conventional ultrasound diagnostics system 11.

2.2. Problems to be Solved by the Invention

However, in cases where a focal distance is selected from among a large number of focal distances corresponding to focal points widely ranging from a shallow portion of the organism to a deep portion of the organism, the number of groups of delay time data required to be stored in advance in the focus memory 19 is extremely increased.

Also, in cases where a tomographic image is produced by converging a group of ultrasonic pulses at many focal points ranging in a depth direction from a shallow portion of the organism to a deep portion of the organism, a focal distance setting operation is required for each of the focal point. Therefore, the number of focal distance setting operations required to produce a frame of tomographic image is extremely increased, and there is a drawback that a frame rate of tomographic images is lowered.

SUMMARY OF THE INVENTION

An object of the present invention is to provide, with due consideration to the drawbacks of such a conventional ultrasound diagnostics system, an ultrasound diagnostics system in which a tomographic image is produced at a high resolution without lowering a frame rate of tomographic images by converging a group of ultrasonic pulses at a small number of focal points widely ranging in a depth direction from a shallow portion of an organism to a deep portion of the organism. Also, the object is to provide a method for obtaining a tomographic image in the ultrasound diagnostics system.

The object is achieved by the provision of an ultrasound diagnostics system comprising:

ultrasonic pulse transmitting and receiving means for transmitting a plurality of ultrasonic pulses to a focal point of an object at one of a plurality of focal distances Fn (n=1,2,--,i,i+1,--,N, and Fi<Fi+1) by delaying each of the ultrasonic pulses according to a particular group of delay time data and receiving a group of echo signals reflected at the focal point of the object, the focal distances Fn satisfying a condition that a focus distance difference Fi+1−Fi is higher than another focus distance difference Fi−Fi−1;

delay time data storing means for storing a plurality of groups of delay time data including the particular group of delay time data used by the ultrasonic pulse transmitting and receiving means, the groups of delay time data corresponding to the focal distances Fn;

delay time data selecting means for selecting the particular group of delay time data from among the groups of delay time data stored in the delay time data storing means;

tomographic data producing means for producing a piece of tomographic image data indicating a portion of a tomographic image from the echo signals received by the ultrasonic pulse transmitting and receiving means;

tomographic image data storing means for storing a plurality of pieces of tomographic image data produced by the tomographic data producing means from the echo signals which are obtained by transmitting the ultrasonic pulses to a plurality of focal points of the object at one or more focal distances; and displaying means for displaying the tomographic image according to the pieces of tomographic image data stored in the tomographic image data storing means.

In the above configuration, a plurality of groups of delay time data are stored in advance in the delay time data storing means. Each of the groups of delay time data indicates a plurality of delay times for a plurality of ultrasonic pulses transmitted to a focal point of the organism at one-to-one correspondence. Therefore, the ultrasonic pulses transmitted can be converged at the focal point of the organism at one of a plurality of focal distances Fn corresponding to the groups of delay time data. Also, the groups of delay time data are produced for the focal distances Fn to satisfy a condition that a focus distance difference Fi+1–Fi is higher than another focus distance difference Fi–Fi–1. For example, the focal distances F are set to satisfy a condition that a ratio (Fi+1–Fi)/(Fi–Fi–1) is equal to a constant value higher than one.

In general, in cases where a tomographic image is produced on condition that a focal point is placed at a shallow portion of an object, the tomographic image reproduces the shallow portion of the object at a high resolution as compared with a tomographic image reproducing a deep portion of the object. Therefore, it is generally required to densely prepare a plurality of groups of delay time data corresponding to the shallow portion of the object for the purpose of making the best use of the tomographic image reproducing the shallow portion of the object at a high resolution. In contrast, because resolution of a tomographic image reproducing the deep portion of the object is not so high, it is not required to densely prepare a plurality of groups of delay time data corresponding to the deep portion of the object.

Because the groups of delay time data are produced for the focal distances Fn to satisfy a condition that a focus distance difference Fi+1–Fi is higher than another focus distance difference Fi–Fi–1, a plurality of groups of delay time data corresponding to the shallow portion of the object can be densely stored in the delay time data storing means. In contrast, a plurality of groups of delay time data corresponding to the deep portion of the object can be sparsely stored in the delay time data storing means.

Therefore, when a group of ultrasonic pulses is transmitted to a plurality of focal points of the object at a plurality of focal distances to produce pieces of tomographic image data indicating a tomographic image, the tomographic image reproducing the focal points ranging from a shallow portion to a deep portion of the object can be displayed at a high resolution by the displaying means. Also, because the tomographic image can be obtained by efficiently using a small number of groups of delay time data, the tomographic image can be displayed by the displaying means without lowering frame rate of tomographic images The object is also achieved by the provision of an ultrasound diagnostics system comprising:

a focus memory for storing a plurality of groups of delay time data corresponding to a plurality of focal distances Fn (n=1,2,--,i,i+1,--,N, and Fi<Fi+1), the focal distances Fn satisfying a condition that a focus distance difference Fi+1–Fi is higher than another focus distance difference Fi–Fi–1;

inputting means for inputting a piece of input information indicating a particular focal distance selected from among the focal distances Fn;

focal distance setting means for reading a particular group of delay time data corresponding to the particular focal distance from the focus memory according to the input information input by the inputting means;

transmitted ultrasonic pulse focusing means for generating a plurality of delaying pulses according to the particular group of delay time data read by the focal distance setting means;

actuating means for generating a plurality of actuating pulses according to the delaying pulses generated by the transmitted ultrasonic pulse focusing means;

an ultrasound probe for generating a plurality of ultrasonic pulses according to the actuating pulses generated by the actuating means to delay the ultrasonic pulses by a plurality of delay times indicated by the particular group of delay time data, transmitting the ultrasonic pulses to a focal point of an object at the particular focal distance and receiving a plurality of echo signals reflected at the focal point of the object;

received echo signal focusing means for delaying the echo signals transmitted from the micro-piezoelectric transducers of the ultrasound probe to converge the echo signals at a fixed time and adding up the echo signals together to produce a summed echo signal;

signal processing means for processing the summed echo signal obtained in the received echo signal focusing means to produce a piece of tomographic image data indicating a portion of a tomographic image;

image data storing means having two-dimensional memories for writing pieces of tomographic image data transmitted from the signal processing means one after another in the two-dimensional memories to store the pieces of tomographic image data indicating the tomographic image; and displaying means for displaying the tomographic image of the object according to the pieces of tomographic image data stored in the image data storing means.

In the above configuration, a particular group of delay time data corresponding to a particular focal distance selected from among the focal distances Fn which satisfy a condition that a focus distance difference Fi+1–Fi is higher than another focus distance difference Fi–Fi–1 is read out from the focus memory according to the input information and is transmitted to the transmitted ultrasonic pulse focusing means, and a plurality of delaying pulses are generated according to the particular group of delay time data and are transmitted to the actuating means. In the actuating means, a plurality of actuating pulses are generated according to the delaying pulses and are transmitted to the ultrasound probe. In the ultrasound probe, a plurality of ultrasonic pulses are generated according to the actuating pulses and are transmitted to an object. In this case, because the ultrasonic pulses are delayed by delay times indicated by the particular group of delay time data, the ultrasonic pulses are converged at a focal point of the object at the particular focal distance.

Thereafter, a plurality of echo signals reflected at the focal point of the object are received by the ultrasound probe, and the echo signals are delayed and added up by the received echo signal focusing means to produce a summed echo signal. The summed echo signal is processed by the signal processing means to produce a piece of tomographic image data indicating a portion of a tomographic image. Therefore, when a group of ultrasonic pulses is converged at each of focal points of the object along a scanning line at the particular focal distance, pieces of tomographic image data along the scanning line are produced. Also, when a group of ultrasonic pulses is repeatedly converged at one or more focal distances, pieces of tomographic image data indicating a tomographic image are produced. The pieces of tomographic image data indicating a tomographic image are stored one after another in the two-dimensional memories of the image data storing means, and the tomographic image of the object is displayed by the displaying means according to the pieces of tomographic image data.

Accordingly, because the focal distances Fn satisfy a condition that a focus distance difference Fi+1–Fi is higher than another focus distance difference Fi–Fi–1, even though a tomographic image corresponding to a plurality of focal points widely ranging in a depth direction from a shallow portion of the object to a deep portion of the object is required, the tomographic image can be displayed by selecting a plurality of groups of delay time data corresponding to a small number of focal distances. That is, the tomographic image can be displayed at a high resolution without lowering a frame rate of tomographic images.

The object is also achieved by the provision of a method for obtaining a tomographic image, comprising the steps of;

preparing a plurality of groups of delay time data corresponding to a plurality of focal distances Fn (n=1,2,—, i,i+1,--,N, and Fi<Fi+1) which satisfy a condition that a focus distance difference Fi+1–Fi is higher than another focus distance difference Fi–Fi–1;

selecting a plurality of particular groups of delay time data from among the groups of delay time data prepared;

converging a plurality of ultrasonic pulses at a focal point of an object at each of a plurality of particular focal distances corresponding to the particular groups of delay time data while delaying the ultrasonic pulses according to each of the particular groups of delay time data;

receiving a plurality of echo signals obtained by reflecting the ultrasonic pulses converged at the focal point of the object at each of the particular focal distances;

producing pieces of tomographic image data indicating a tomographic image from the echo signals; and displaying the tomographic image according to the pieces of tomographic image data.

In the above steps, because the focal distances Fn satisfy a condition that a focus distance difference Fi+1–Fi is higher than another focus distance difference Fi–Fi–1, even though a tomographic image corresponding to a plurality of focal points widely ranging in a depth direction from a shallow portion of the object to a deep portion of the object is required, the tomographic image can be displayed by selecting a plurality of particular groups of delay time data corresponding to a small number of particular focal distances. That is, the tomographic image can be displayed at a high resolution without lowering a frame rate of tomographic images.

BRIEF DESCRIPTION OF THE DRAWINGS

The objects, features and advantages of the present invention will be apparent from the following description taken in conjunction with the accompanying drawings, in which.

DETAIL DESCRIPTION OF THE EMBODIMENTS

Preferred embodiments of an ultrasound diagnostics system and a tomographic image obtaining method according to the present invention are described with reference to drawings.

Figure 3:
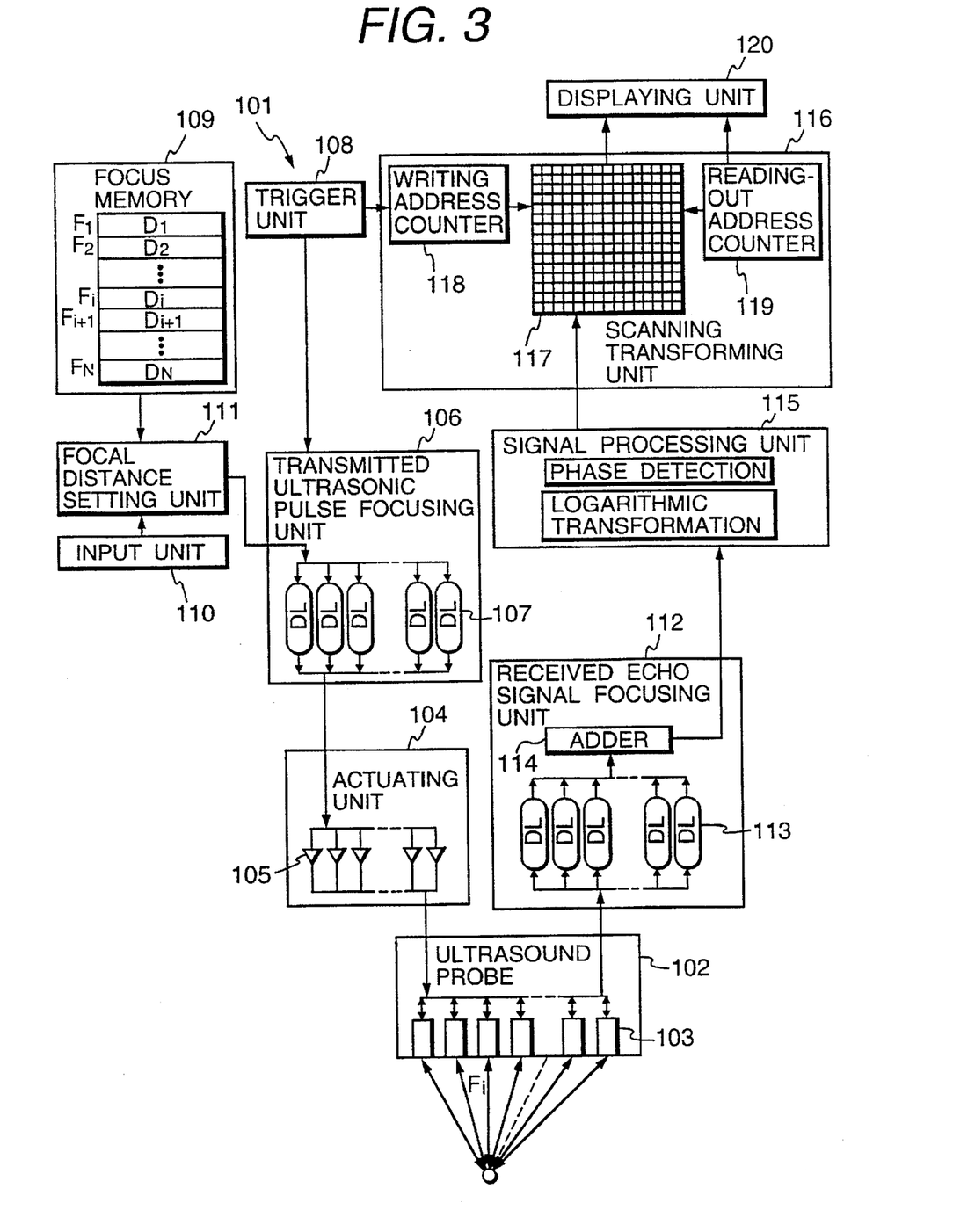
FIG. 3 is a block diagram of an ultrasound diagnostics system according to a first embodiment of the present invention.

FIG. 3 is a block diagram of an ultrasound diagnostics system according to a first embodiment of the present invention.

As shown in FIG. 3, an ultrasound diagnostics system 101 comprises an ultrasound probe 102 having a plurality of micro-piezoelectric transducers 103 for transmitting a group of ultrasonic pulses from the transducers 103 to an object such as an organism at a special convergence while scanning the organism along a scanning line and receiving a group of echo signals reflected in the organism to the transducers 103, an actuating unit 104 having a plurality of pulse oscillators 105 for actuating the micro-piezoelectric transducers 103 of the ultrasound probe 102 with a plurality of actuating pulses transmitted from the pulse oscillators 105, a transmitted ultrasonic pulse focusing unit 106 having a plurality of delaying circuits 107 for transmitting a plurality of delaying pulses Tx generated in the delaying circuits 107 to the pulse oscillators 105 to delay the generation of the actuating pulses for the purpose of converging the group of ultrasonic pulses transmitted from the micro-piezoelectric transducers 103 at a focal point of the organism at the special convergence, a trigger unit 108 for transmitting a trigger pulse Tg to the transmitted ultrasonic pulse focusing unit 106 to trigger the generation of the delaying pulses Tx, a focus memory 109 for storing a plurality of groups of special delay time data Dn (n=1 to N) corresponding to a plurality of special focal distances Fn, an inputting unit 110 for inputting a piece of input information indicating a desired special focal distance Fi, a focal distance setting unit 111 for reading a group of special delay time data Di from the focus memory 109 according to the input information and transmitting the group of special delay time data Di to the transmitted ultrasonic pulse focusing unit 106 to set the convergence of the group of ultrasonic pulses at a focal point of the organism corresponding to the special focal distance Fi, a received echo signal focusing unit 112 having a plurality of delaying circuits 113 and an adder 114 for delaying the echo signals transmitted from the micro-piezoelectric transducers 103 of the ultrasound probe 102 at a plurality of time differences in the delaying circuits 113 to converge the echo signals at a fixed time and adding the echo signals together in the adder 114 to produce a summed echo signal Se, a signal processing unit 115 for performing a logarithmic transformation for the summed echo signal Se obtained in the received echo signal focusing unit 112 and detecting a phase of the summed echo signal Se to produce a piece of tomographic image data indicating a portion of a tomographic image, a scanning transformation unit 116 having two-dimensional memories 117, a write address counter 118 and a read address counter 119 for writing the piece of tomographic image data transmitted from the signal processing unit 115 in each of the two-dimensional memories 117 according to a write address signal of the write address counter 118 transmitted in synchronization with the trigger signal Tg of the trigger unit 108 and producing an image signal Sv indicating the tomographic image expressed by a displaying format such as a television format, and a displaying unit 120 for displaying the ultrasound tomographic image of the organism according to the image signal Sv, which is read out from the two-dimensional memories 117 according to a read address of the read address counter 119, in synchronization with a synchronizing signal transmitted from the read address counter 119.

A determining method of the special focal distances Fn to which the groups of special delay time data Dn stored in the focus memory 109 correspond is described.

Figure 4A:
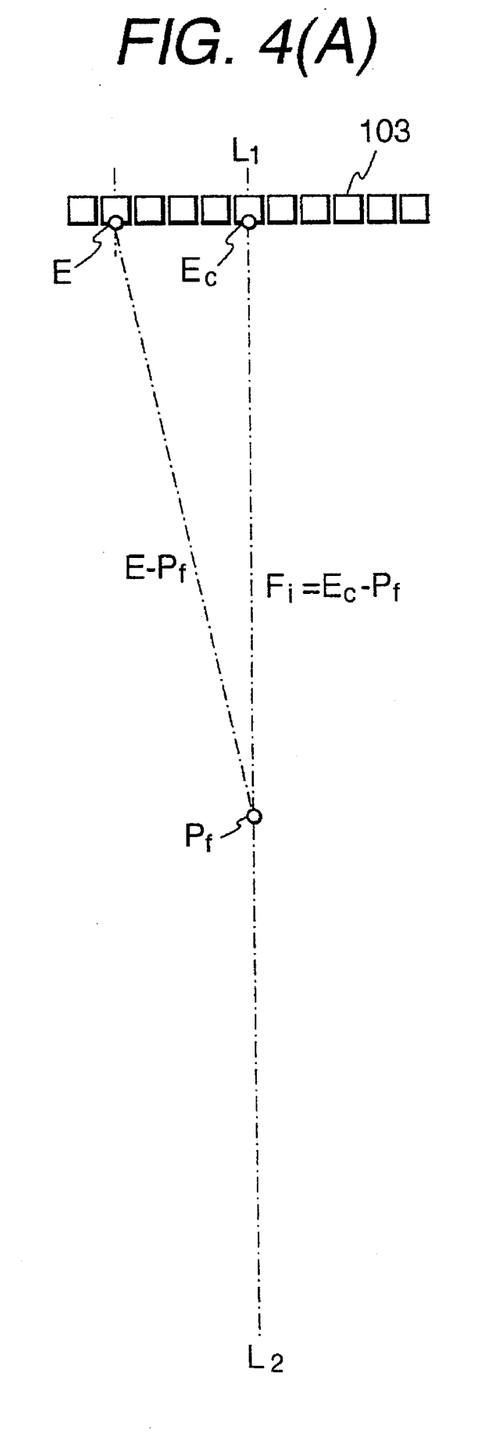
FIG. 4(A) shows a general principle for converging a group of ultrasonic waves (or a group of ultrasonic pulses) at a focal point placed on a central line L1–L2 in an electronic scanning type ultrasound diagnostics system.

FIG. 4(A) shows a general principle for converging a group of ultrasonic waves (or a group of ultrasonic pulses) at a focal point Pf in an electronic scanning type ultrasound diagnostics system.

As shown in FIG. 4(A), a central micro-piezoelectric transducer 103 arranged closest to a focal point Pf corresponding to a special focal distance Fi is selected from among the micro-piezoelectric transducers 103 arranged in alignment. A position of the central micro-piezoelectric transducer 103 is indicated by a symbol Ec. Thereafter, the central micro-piezoelectric transducer 103 and a plurality of particular micro-piezoelectric transducers 103 arranged symmetrically with respect to the central micro-piezoelectric transducer 103 are used to output the ultrasonic waves. A position of one of the particular micro-piezoelectric transducers 103 is indicated by a symbol E. A distance from the position Ec to the focal point Pf is indicated by Ec–Pf, and a distance from the position E to the focal point Pf is indicated by E–Pf. The distance Ec–Pf is equal to the special focal distance Fi. In this case, a special delay time for the particular micro-piezoelectric transducer 103 placed at the position E is defined as a difference between a transmitting time of an ultrasonic wave transmitting the distance E–Pf and a transmitting time of an ultrasonic wave transmitting the distance Ec–Pf. Therefore, the special delay times for the particular micro-piezoelectric transducers 103 are stored in the focus memory 109 as a group of special delay time data Di corresponding to the special focal distance Fi.

In general, in cases where a tomographic image is produced on condition that a focal point is placed at a shallow portion of an organism, the tomographic image reproduces the shallow portion of the organism at a high resolution as compared with a tomographic image reproducing a deep portion of the organism. Therefore, it is required to densely prepare a plurality of groups of delay time data corresponding to the shallow portion of the organism for the purpose of making the best use of the tomographic image reproducing the shallow portion of the organism at a high resolution. In contrast, because resolution of a tomographic image reproducing a deep portion of the organism is not so high, it is not required to densely prepare a plurality of groups of delay time data corresponding to the deep portion of the organism.

Figure 4B:
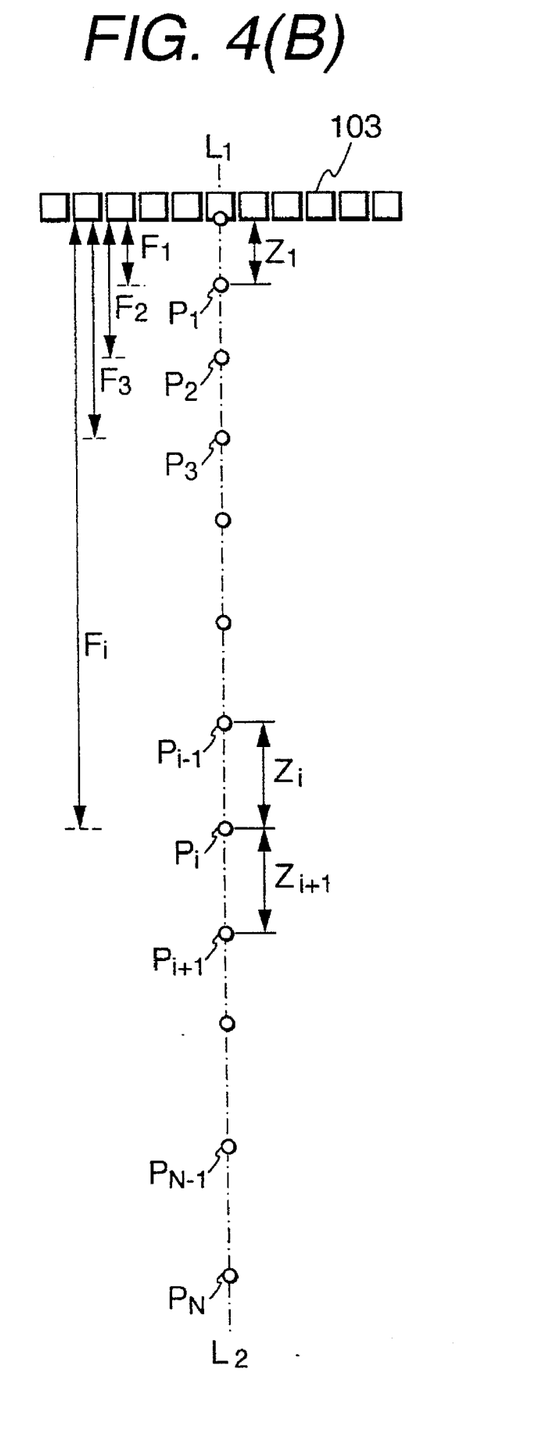
FIG. 4(B) shows a plurality of focus points Pn arranged on a central line L1–L2 with a special regularity.

FIG. 4(B) shows a plurality of focus points Pn arranged on a central line L1–L2 with a special regularity.

As shown in FIG. 4(B), a focus distance difference between two focal points Pi–1 and Pi adjacent to each other is indicated by a symbol Zi. The focus distance difference Zi is equal to a value Fi–Fi–1. In this embodiment, the special focal distances Fn are determined as follows.

$1 < Z2/Z1 = Z3/Z2 = --- = Zi/Zi-1 = --- = ZN/ZN-1$

That is, a ratio $Zi/Zi-1$ of a focus distance difference $Zi$ to another focus distance difference $Zi-1$ is set to a constant value higher than one.

Figure 5:
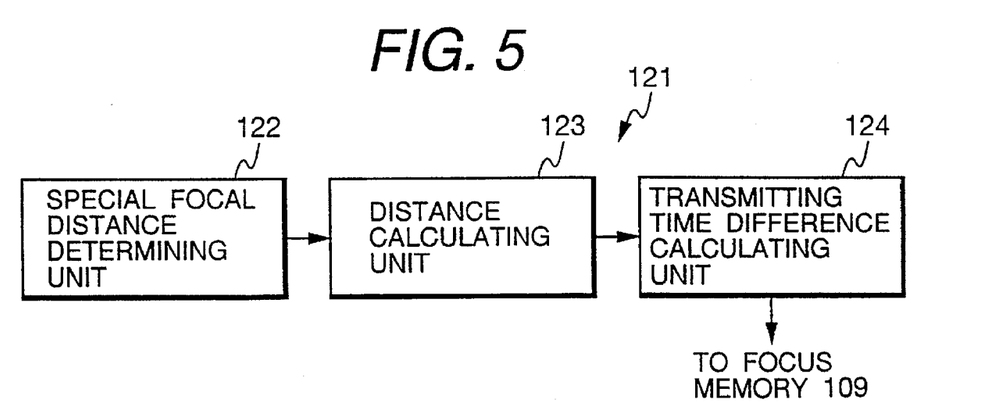
FIG. 5 shows a block diagram of a special delay time data producing apparatus which is additionally included in the ultrasound diagnostics system shown in FIG. 3.

FIG. 5 shows a block diagram of a special delay time data producing apparatus which is additionally included in the ultrasound diagnostics system 101.

As shown in FIG. 5, a special delay time data producing apparatus 121 comprises a special focal distance determining unit 122 for determining the special focal distances Fn to set a ratio $(Fi-Fi-1)/(Fi-1-Fi-2)$ to a constant value higher than one, a distance calculating unit 123 for calculating a transmitting distance between each of the particular micro-piezoelectric transducers 103 and a focal point corresponding to a special focal distance Fi determined by the special focal distance determining unit 122 for each of the special focal distances Fn, and a transmitting time difference calculating unit 124 for calculating a transmitting time difference between a transmitting time of an ultrasonic pulse transmitting each of the transmitting distances calculated by the distance calculating unit 123 and a reference transmitting time of an ultrasonic pulse transmitting the special focal distance Fi for each of the special focal distances Fn. The transmitting time differences calculated by the transmitting time difference calculating unit 124 are stored in the focus memory 109 as the groups of special delay time data Dn.

After the groups of special delay time data Dn are stored in the focus memory 109, a group of ultrasonic pulses is converged at a focal point of the organism corresponding to a special focal distance Fi by the ultrasound prove 102 in the same manner as in the system 11. Thereafter, pieces of tomographic image data indicating a tomographic image are stored in the two-dimensional memories 117 of the scanning transformation unit 116, and the tomographic image is displayed by the displaying unit 120 in the same manner as in the system 11.

Accordingly, because the groups of special delay time data Dn produced on condition that the special focal distances Fn are determined to set a ratio $(Fi-Fi-1)/(Fi-1-Fi-2)$ to a constant value higher than one are stored in the focus memory 109, a relationship $Zi < Zi+1$ in the focus distance differences Zn is satisfied, the groups of special delay time data Dn corresponding to a shallow portion of the organism can be densely prepared, and the groups of special delay time data Dn corresponding to a deep portion of the organism can be sparsely prepared. Therefore, even though a tomographic image corresponding to a plurality of focal points widely ranging in a depth direction from the shallow portion of the organism to the deep portion of the organism is required, the tomographic image can be displayed by the displaying unit 120 by selecting a plurality of groups of special delay time data corresponding to a small number of special focal distances. That is, the tomographic image can be displayed at a high resolution without lowering a frame rate of tomographic images.

Next, an example of the selection of a plurality of particular groups of delay time data Dn at every M groups from the focus memory 109 is described.

Figure 6A:
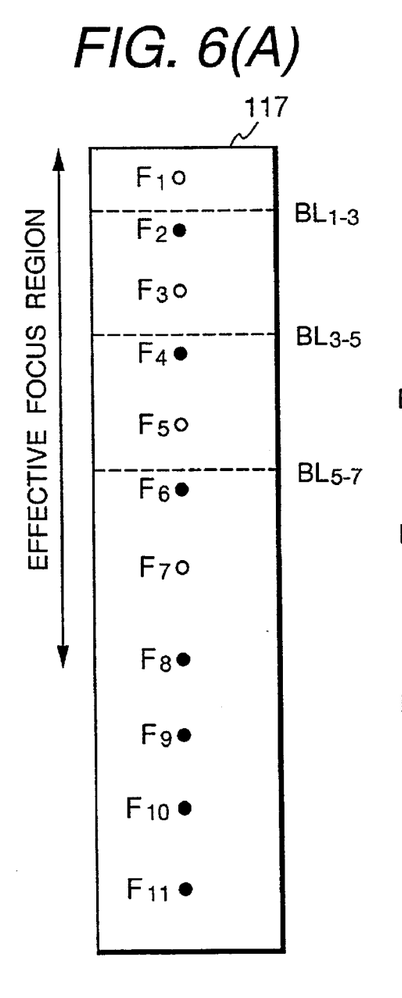
FIG. 6(A) shows two-dimensional memories shown in FIG. 3 in which pieces of tomographic image data indicating a tomographic image obtained by combining a first portion of tomographic image corresponding to a special focal distance F1, a second portion of tomographic image corresponding to a special focal distance F3, a third portion of tomographic image corresponding to a special focal distance F5 and a fourth portion of tomographic image corresponding to a special focal distance F7 are stored.

FIG. 6(A) shows the two-dimensional memories 117 in which pieces of tomographic image data indicating a tomographic image obtained by combining a first portion of tomographic image corresponding to a special focal distance F1, a second portion of tomographic image corresponding to a special focal distance F3, a third portion of tomographic image corresponding to a special focal distance F5 and a fourth portion of tomographic image corresponding to a special focal distance F7 are stored.

As shown in FIG. 6(A), in cases where a plurality of particular focal distances mainly representing a plurality of focal points at a shallow portion of the organism are selected from among the special focal distances Fn at every two (M=2) focal distances, a plurality of groups of tomographic image data which each correspond to one of the particular focal distances and indicate a portion of tomographic image are written in a plurality of memory regions of the memories 117 in a depth order. That is, pieces of tomographic image data indicating a first portion of tomographic image corresponding to a special focal distance F1 are stored in a first memory region placed at a top portion of the memories 117 partitioned by a boundary line BL1-3, pieces of tomographic image data indicating a second portion of tomographic image corresponding to a special focal distance F3 (F3>F1) are stored in a second memory region placed between the boundary line BL1-3 and a boundary line BL3-5, pieces of tomographic image data indicating a third portion of tomographic image corresponding to a special focal distance F5 (F5>F1) are stored in a third memory region placed between the boundary line BL3-5 and a boundary line BL5-7, and pieces of tomographic image data indicating a fourth portion of tomographic image corresponding to a special focal distance F7 (F7>F5) are stored in a fourth memory region placed at a bottom portion of the memories 117 partitioned by the boundary line BL5-7.

Therefore, in cases where an operator intends to select a plurality of special focal distances mainly representing a plurality of focal points at a shallow portion of the organism, the special focal distances F1, F3, F5 and F7 close to each other can be selected by the operator in a short effective focus region.

Figure 6B:
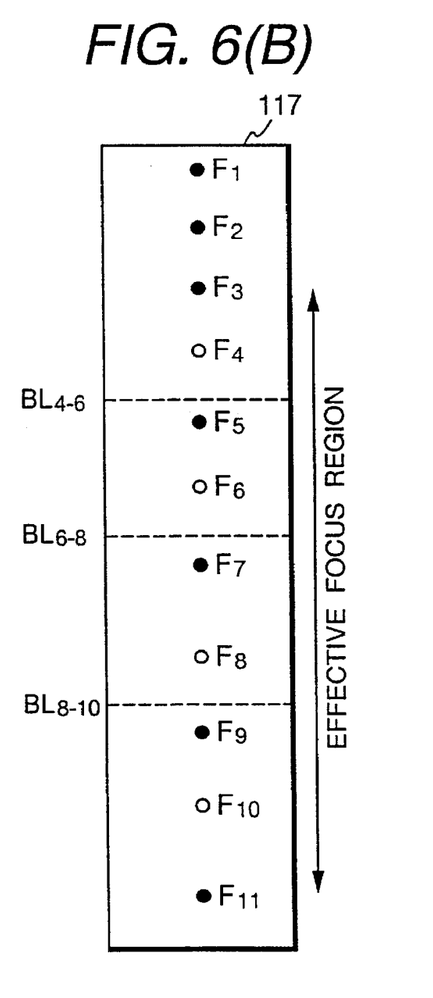
FIG. 6(B) shows the two-dimensional memories shown in FIG. 3 in which pieces of tomographic image data indicating a tomographic image obtained by combining a first portion of tomographic image corresponding to a special focal distance F4, a second portion of tomographic image corresponding to a special focal distance F6, a third portion of tomographic image corresponding to a special focal distance F8 and a fourth portion of tomographic image corresponding to a special focal distance F10 are stored.

FIG. 6(B) shows the two-dimensional memories 117 in which pieces of tomographic image data indicating a tomographic image obtained by combining a first portion of tomographic image corresponding to a special focal distance F4, a second portion of tomographic image corresponding to a special focal distance F6, a third portion of tomographic image corresponding to a special focal distance F8 and a fourth portion of tomographic image corresponding to a special focal distance F10 are stored.

As shown in FIG. 6(B), in cases where a plurality of particular focal distances mainly representing a plurality of focal points at a deep portion of the organism are selected from among the special focal distances Fn at every two (M=2) focal distances, a plurality of groups of tomographic image data which each correspond to one of the particular focal distances and indicate a portion of tomographic image are written in a plurality of memory regions of the memories 117 in a depth order. That is, pieces of tomographic image data indicating a first portion of tomographic image corresponding to a special focal distance F4 are stored in a first memory region placed at a top portion of the memories 117 partitioned by a boundary line BL4-6, pieces of tomographic image data indicating a second portion of tomographic image corresponding to a special focal distance F6 (F6>F4) are stored in a second memory region placed between the boundary line BL4-6 and a boundary line BL6-8, pieces of tomographic image data indicating a third portion of tomographic image corresponding to a special focal distance F8 (F8>F6) are stored in a third memory region placed between the boundary line BL6-8 and a boundary line BL8-9, and pieces of tomographic image data indicating a fourth portion of tomographic image corresponding to a special focal distance F10 (F10>F8) are stored in a fourth memory region placed at a bottom portion of the memories 117 partitioned by the boundary line BL8-9.

Therefore, in cases where an operator intends to select a plurality of special focal distances mainly representing a plurality of focal points at a deep portion of the organism, the special focal distances F4, F6, F8 and F10 spaced far from each other can be selected by the operator in a long effective focus region.

Accordingly, in cases where a tomographic image is produced according to a combination of a plurality of special focal distances, the operator can be select a plurality of special focal distances close to each other for a shallow portion of the organism in which an effective focus region is short, and the operator can be select a plurality of special focal distances spaced far from each other for a deep portion of the organism in which an effective focus region is long. Therefore, even though a tomographic image corresponding to a plurality of focal points widely ranging in a depth direction from the shallow portion of the organism to the deep portion of the organism is required, the tomographic image can be displayed by selecting a plurality of special groups of delay time data corresponding to a small number of special focal distances. That is, the tomographic image can be displayed at a high resolution without lowering a frame rate of tomographic images.

In the first embodiment, the groups of special delay time data Dn stored in the focus memory 109 are prepared for the special focal distances Fn to satisfy a condition that a ratio (Fi−Fi−1)/(Fi−1−Fi−2) is equal to a constant value higher than one. However, because a condition that the groups of special delay time data Dn corresponding to the shallow portion of the organism are densely prepared is required, it is applicable that the focal distances Fn satisfy a condition that a focus distance difference Fi+1−Fi is higher than another focus distance difference Fi−Fi−1.

Having illustrated and described the principles of the present invention in a preferred embodiment thereof, it should be readily apparent to those skilled in the art that the invention can be modified in arrangement and detail without departing from such principles. We claim all modifications coming within the spirit and scope of the accompanying claims.

What is claimed is:

1. An ultrasound diagnostics system comprising:
   ultrasonic pulse transmitting and receiving means for transmitting a plurality of ultrasonic pulses to a focal point of an object at one of a plurality of focal distances Fn (n=1,2,3,--,N, and Fn<Fn+1) and by delaying each of the ultrasonic pulses according to a particular group of delay time data and receiving a group of echo signals reflected at the focal point of the object, the focal distances Fn satisfying a condition that a focus distance difference Fi+1−Fi (i is a natural number equal to or lower than N−1) is higher than a focus distance difference Fi−Fi−1 and the focus distance difference Fi−Fi−1 is higher than a focus distance difference Fi−1−Fi−2;

delay time data storing means for storing a plurality of groups of delay time data including the particular group of delay time data used by the ultrasonic pulse transmitting and receiving means, the groups of delay time data corresponding to the focal distances Fn;

delay time data selecting means for selecting the particular group of delay time data from among the groups of delay time data stored in the delay time data storing means;

tomographic data producing means for producing a piece of tomographic image data indicating a portion of a tomographic image from the echo signals received by the ultrasonic pulse transmitting and receiving means;

tomographic image data storing means for storing a plurality of pieces of tomographic image data produced by the tomographic data producing means from the echo signals which are obtained by transmitting the ultrasonic pulses to a plurality of focal points of the object at one or more focal distances; and displaying means for displaying the tomographic image according to the pieces of tomographic image data stored in the tomographic image data storing means.

2. An ultrasound diagnostics system according to claim 1, wherein the groups of delay time data stored in the delay time data storing means are prepared for the focal distances Fn to satisfy a condition that a plurality of ratios (Fn−Fn−1)/(Fn−1−Fn−2) are respectively equal to a constant value higher than one.

3. An ultrasound diagnostics system according to claim 1, further comprising;

inputting means for inputting pieces of input information indicating a plurality of particular focal distances selected form among the focal distances Fn at every M (M is a natural number) focal distances, a plurality of particular groups of delay time data corresponding to the particular focal distances being reading out from the delay time data storing means and being selected by the delay time data selecting means; and the tomographic image data storing means comprises a plurality of memory regions for storing a plurality of pieces of tomographic image data corresponding to the particular focal distances in a depth order, a tomographic image composed of a plurality of portions which correspond to the particular focal distances in the depth order being displayed by the displaying means.

4. An ultrasound diagnostics system according to claim 1, wherein the ultrasonic pulse transmitting and receiving means comprises a plurality of piezoelectric transducers for respectively transmitting one of the ultrasonic pulses and receiving one of the echo signals, and the ultrasound diagnostics system further comprising;

focal distance determining means for determining the focal distances Fn on condition that the focus distance difference Fi+1−Fi is higher than the other focus distance difference Fi−F−1 and the focus distance difference Fi−Fi−1 is higher than the focus distance difference Fi−1−Fi−2;

distance calculating means for calculating a transmitting distance between each of the piezoelectric transducers and a focal point of the object corresponding to one of the focal distances Fn determined by the focal determining means for each of the focal distances Fn; and transmitting time difference calculating means for calculating a transmitting time difference between a transmitting time of an ultrasonic pulse transmitting one transmitting distance calculated by the distance calculating means and a reference transmitting time of an ultrasonic pulse transmitting one of the focal distances Fn corresponding to the transmitting distance for each of the transmitting distances, the transmitting time differences corresponding to each of the focal distances Fn being stored in the delay time data storing means as a group of delay time data corresponding to each of the focal distances Fn.

5. An ultrasound diagnostics system comprising:

a focus memory for storing a plurality of groups of delay time data corresponding to a plurality of focal distances Fn (n=1,2,3,--,N, and Fn<Fn+1), the focal distances Fn satisfying a condition that a focus distance difference Fi+1−Fi (i is a natural number equal to or lower than N−1) is higher than a focus distance difference Fi−Fi−1 and the focus distance difference Fi−Fi−1 is higher than a focus distance difference Fi−1−Fi−2;

inputting means for inputting a piece of input information indicating a particular focal distance selected from among the focal distances Fn;

focal distance setting means for reading a particular group of delay time data corresponding to the particular focal distance from the focus memory according to the input information input by the inputting means;

transmitted ultrasonic pulse focusing means for generating a plurality of delaying pulses according to the particular group of delay time data read by the focal distance setting means;

actuating means for generating a plurality of actuating pulses according to the delaying pulses generated by the transmitted ultrasonic pulse focusing means;

an ultrasound probe for generating a plurality of actuating pulses according to the delay pulses generated by the transmitted ultrasonic pulse focusing means;

an ultrasound probe for generating a plurality of ultrasonic pulses according to the actuating pulses generated by the actuating means to delay the ultrasonic pulses by the plurality of delay times indicated by the particular group of delay time data, transmitting the ultrasonic pulses to a focal point of an object at the particular focal distance and receiving a plurality of echo signals reflected at the focal point of the object;

received echo signal focusing means for delaying the echo signals transmitted from the micro-piezoelectric transducers of the ultrasound probe to converge the echo signals at a fixed time and adding up the echo signals together to produce a summed echo signal;

signal processing means for processing the summed echo signal obtained in the received echo signal focusing means to produce a piece of tomographic image data indicating a portion of a tomographic image;

image data storing means having two-dimensional memories for writing pieces of tomographic image data transmitted from the signal processing means one after another in the two-dimension al memories to store the pieces of tomographic image data indicating the tomographic; and displaying means for displaying the tomographic image of the object according to the pieces of tomographic image data stored in the image data storing means.

6. An ultrasound diagnostics system according to claim 5, wherein the groups of delay time data stored in the focus memory are prepared for the focal distances Fn to satisfy a condition that a plurality of ratios (Fn–Fn–1)/(Fn–1–Fn–2) are respectively equal to a constant value higher than one.

7. An ultrasound diagnostics system according to claim 5, wherein pieces of input information indicating a plurality of particular focal distances selected from among the focal distances Fn at every M (M is a natural number) focal distances are input by the inputting means, the two-dimensional memories of the image data storing means are partitioned into a plurality of memory regions for storing a plurality of pieces of tomographic image data corresponding to the particular focal distances in a depth order, and a tomographic image composed of a plurality of portions which correspond to the particular focal distances in the depth order is displayed by the displaying means.

8. An ultrasound diagnostics system according to claim 5, wherein the ultrasound probe comprises a plurality of piezoelectric transducers for respectively transmitting one of the ultrasonic pulses and receiving one of the echo signals, and the ultrasound diagnostics system further comprising:

focal distance determining means for determining the focal distances Fn on condition that the focus distance difference Fi+1–Fi is higher than the other focus distance difference Fi–Fi–1 and the focus distance difference Fi–F–1 is higher than the focus distance difference Fi–1–Fi–2;

distance calculating means for calculating a transmitting distance between each of the piezoelectric transducers and a focal point of the object corresponding to one of the focal distance Fn determined by the focal distance determining means for each of the focal distances Fn; and transmitting time difference calculating means for calculating a transmitting time difference between a transmitting time of an ultrasonic pulse transmitting one transmitting distance calculated by the distance calculating means and a reference transmitting time of an ultrasonic pulse transmitting one of the focal distances Fn corresponding to the transmitting distance for each of the transmitting distances, the transmitting time differences corresponding to each of the focal distances Fn being stored in the focal memory as a group of delay time data corresponding to each of the focal distances Fn.

9. A method for obtaining a tomographic image, comprising the steps of;

preparing a plurality of groups of delay time data corresponding to a plurality of focal distances Fn (n=1,2,3, --,N, and Fn<Fn+1), which satisfy a condition that a focus distance difference Fi+1–Fi (i is a natural number equal to or lower than N–1) is higher than a focus distance difference Fi–Fi–1 and the focus distance difference Fi–Fi–1 is higher than a focus distance difference Fi–1–Fi–2;

selecting a plurality of particular groups of delay time data from among the groups of delay time data prepared;

converging a plurality of ultrasonic pulses at a focal point of an object at each of a plurality of particular focal distances corresponding to the particular groups of delay time data while delaying the ultrasonic pulses according to each of the particular groups of delay time data;

receiving a plurality of echo signals obtained by reflecting the ultrasonic pulses converged at the focal point of the object at each of the particular focal distances;

producing pieces of tomographic image data indicating a tomographic image from the echo signals; and displaying the tomographic image according to the pieces of tomographic image data.

10. A method according to claim 9, the step of preparing a plurality of groups of delay time data comprising the step of:

setting the focal distances Fn to satisfy a condition that a plurality of ratios (Fn–Fn–1)/(Fn–1–Fn–2) are respectively equal to a constant value higher than one.

11. A method according to claim 9, further comprising the steps of:

inputting pieces of input information indicating the particular focal distances selected from among the focal distances Fn at every M (M is a natural number) focal distances to select the particular groups of delay time data corresponding to the particular focal distances indicated by the input information in the step of selecting a plurality of particular groups of delay time data; and arranging the pieces of tomographic image data corresponding to the particular focal distances in two-dimensional memories in order of focal distance, and the step of displaying the tomographic image including;

displaying the tomographic image composed of a plurality of portions of tomographic image arranged in order of depth of the object.

* * * * *